United States Patent
Rinaldi et al.

(10) Patent No.: US 6,553,095 B2
(45) Date of Patent: Apr. 22, 2003

(54) AUTOMATIC EXPOSURE CONTROL FOR DENTAL PANORAMIC AND CEPHALOGRAPHIC X-RAY EQUIPMENT

(75) Inventors: Gerardo Rinaldi, Milan (IT); Giuseppe Rotondo, Milan (IT); Gianfranco Venturino, Milan (IT)

(73) Assignee: Dentsply Research & Development Corp

( * ) Notice: Subject to any disclaimer, the term of this patent is extended or adjusted under 35 U.S.C. 154(b) by 0 days.

(21) Appl. No.: 10/024,873

(22) Filed: Dec. 19, 2001

(65) Prior Publication Data

US 2002/0085673 A1 Jul. 4, 2002

Related U.S. Application Data

(63) Continuation of application No. 09/679,768, filed on Oct. 5, 2000.
(60) Provisional application No. 60/158,706, filed on Oct. 8, 1999.

(51) Int. Cl.$^7$ ................................................. H05G 1/26
(52) U.S. Cl. ...................................... 378/108; 378/109
(58) Field of Search ............................. 378/108, 109, 378/111

(56) References Cited

U.S. PATENT DOCUMENTS

| 3,894,235 A | 7/1975 | Franke | 250/402 |
|---|---|---|---|
| 3,911,273 A | 10/1975 | Franke | 250/322 |

(List continued on next page.)

FOREIGN PATENT DOCUMENTS

| CA | 1259711 | 9/1989 |
|---|---|---|
| DE | 196 48 076 | 5/1997 |
| DE | 44 33 545 | 11/1997 |
| DE | 196 48 052 | 6/1998 |
| DE | 197 54 463 | 6/1998 |
| DE | 42 38 268 | 7/1998 |
| DE | 197 31 927 | 2/1999 |
| DE | 197 34 717 | 2/1999 |
| EP | 0 229 497 | 7/1987 |
| EP | 0 373 717 | 6/1990 |
| EP | 0 234 603 | 7/1992 |
| EP | 0 415 075 | 10/1994 |
| EP | 0 408 167 | 9/1995 |
| EP | 0 673 623 | 9/1995 |
| EP | 0 685 201 | 12/1995 |
| EP | 0 574 368 | 4/1997 |
| EP | 0 776 149 | 5/1997 |
| EP | 0 632 994 | 1/1999 |
| EP | 0 858 773 | 3/1999 |
| EP | 0 632 995 | 4/1999 |
| EP | 0 634 671 | 8/1999 |
| GB | 2304017 | 11/1999 |
| JP | 62 222 780 | 9/1987 |
| JP | 3 109 057 | 5/1991 |
| WO | 89/07322 | 8/1989 |

(List continued on next page.)

Primary Examiner—Robert H. Kim
Assistant Examiner—Hoon K. Song
(74) Attorney, Agent, or Firm—Douglas J. Hura; James B. Bieber (57) ABSTRACT

An apparatus and method used in dental panoramic and cephalographic x-ray equipment provides automatic adjustment of the pre-programmed exposure factors in order to obtain optimisation of the grey scale of the latent image on various kinds of x-ray detectors, such as the radiographic film or x-ray image detector plates. A sensor, such as photo diodes, detects the intensity of the radiation passed through the patient and incident on the x-ray detector and feeds it to a control unit. The control unit provides a computed simulation of the latent image grey level and adjusts the programmed exposure factors in order to establish the grey level of the latent image at the required reference value.

12 Claims, 5 Drawing Sheets

U.S. PATENT DOCUMENTS

| | | | | |
|---|---|---|---|---|
| 3,974,385 A | 8/1976 | Grim | 250/402 |
| 3,987,281 A | 10/1976 | Hodes | 235/151.3 |
| 3,991,314 A | 11/1976 | Schmitman et al. | 250/402 |
| 4,021,672 A | 5/1977 | Franke | 250/402 |
| 4,061,920 A | 12/1977 | Mollendorf et al. | 250/413 |
| 4,070,578 A | 1/1978 | Timothy et al. | 250/336 |
| 4,097,741 A | 6/1978 | Pfeiler et al. | 250/322 |
| 4,104,531 A | 8/1978 | Weiss | 250/490 |
| 4,158,138 A * | 6/1979 | Hellstrom | 250/402 |
| 4,160,906 A | 7/1979 | Daniels et al. | 250/322 |
| 4,160,997 A | 7/1979 | Schwartz | 358/93 |
| 4,188,537 A | 2/1980 | Franke | 250/416 |
| 4,247,780 A | 1/1981 | Webber et al. | 250/491 |
| 4,259,582 A | 3/1981 | Albert | 25/102 |
| 4,352,987 A | 10/1982 | Hayashi et al. | 378/150 |
| 4,454,606 A | 6/1984 | Relihan | 378/97 |
| 4,475,224 A | 10/1984 | Grassme | 378/38 |
| 4,486,896 A | 12/1984 | Richter et al. | 378/108 |
| 4,495,632 A | 1/1985 | Nakano | 378/40 |
| 4,501,010 A | 2/1985 | Grassme | 378/38 |
| 4,589,121 A | 5/1986 | Makino | 378/39 |
| 4,641,331 A | 2/1987 | Makino et al. | 378/108 |
| 4,675,888 A | 6/1987 | Gastrin | 378/38 |
| 4,741,007 A | 4/1988 | Virta et al. | 378/39 |
| 4,783,793 A | 11/1988 | Virta et al. | 378/39 |
| 4,797,905 A | 1/1989 | Ochmann | 378/108 |
| 4,811,372 A | 3/1989 | Doebert et al. | 378/39 |
| 4,813,060 A | 3/1989 | Heubeck et al. | 378/39 |
| 4,815,115 A | 3/1989 | Nieminen et al. | 378/38 |
| 4,823,369 A | 4/1989 | Guenther et al. | 378/22 |
| 4,847,881 A | 7/1989 | Heubeck | 378/38 |
| 4,856,038 A | 8/1989 | Guenther et al. | 378/39 |
| 4,878,234 A | 10/1989 | Pfeiffer et al. | 378/40 |
| 4,905,265 A | 2/1990 | Cox et al. | 378/99 |
| 4,930,146 A | 5/1990 | Flakas et al. | 378/110 |
| 4,980,905 A | 12/1990 | Meccariello | 378/207 |
| 4,985,907 A | 1/1991 | Moteni | 378/139 |
| 4,995,062 A | 2/1991 | Schulze-Ganzlin et al. | 378/22 |
| 5,005,195 A | 4/1991 | Lanza et al. | 378/62 |
| 5,018,177 A | 5/1991 | McDavid et al. | 378/62 |
| 5,043,582 A | 8/1991 | Cox et al. | 250/370.09 |
| 5,090,040 A | 2/1992 | Lanza et al. | 378/62 |
| 5,090,047 A | 2/1992 | Angotti et al. | 378/170 |
| 5,093,852 A | 3/1992 | Nishikawa et al. | 378/39 |
| 5,195,114 A | 3/1993 | Sairenji et al. | 378/40 |
| 5,214,686 A | 5/1993 | Webber | 378/38 |
| 5,267,296 A | 11/1993 | Albert | 378/113 |
| 5,293,312 A | 3/1994 | Waggener | 364/413.21 |
| 5,331,166 A | 7/1994 | Yamamoto et al. | 250/370.11 |
| 5,386,448 A | 1/1995 | Tammisalo et al. | 378/38 |
| D355,964 S | 2/1995 | Nelvig | D24/158 |
| 5,425,065 A | 6/1995 | Jarvenin | 378/40 |
| 5,434,418 A | 7/1995 | Schick | 250/370.11 |
| 5,454,022 A | 9/1995 | Lee et al. | 378/98.8 |
| 5,473,660 A | 12/1995 | Bastiaens et al. | 378/98.8 |
| 5,490,197 A | 2/1996 | Albert et al. | 378/113 |
| 5,511,106 A | 4/1996 | Doebert et al. | 378/146 |
| 5,513,252 A | 4/1996 | Blaschka et al. | 378/98.8 |
| 5,519,437 A | 5/1996 | Nelvig | 348/162 |
| 5,519,751 A | 5/1996 | Yamamoto et al. | 378/98.8 |
| 5,541,974 A | 7/1996 | Sklebitz | 378/98.8 |
| 5,579,366 A | 11/1996 | Docbert et al. | 378/189 |
| 5,583,905 A | 12/1996 | Nishiki et al. | 378/98.8 |
| 5,600,699 A | 2/1997 | Suzuki et al. | 378/38 |
| 5,602,896 A | 2/1997 | Diepstraten | 378/98.7 |
| 5,608,455 A | 3/1997 | Oda | 348/245 |
| 5,617,462 A | 4/1997 | Spratt | 378/98.7 |
| 5,625,662 A | 4/1997 | Toth et al. | 378/16 |
| 5,640,018 A | 6/1997 | Suzuki et al. | 250/368 |
| 5,663,998 A | 9/1997 | Suzuki et al. | 378/62 |
| 5,664,001 A | 9/1997 | Tachibana et al. | 378/98.8 |
| 5,668,375 A | 9/1997 | Petrick et al. | 250/370.09 |
| 5,677,940 A | 10/1997 | Suzuki et al. | 378/38 |
| 5,694,448 A | 12/1997 | Morcom | 378/98.8 |
| 5,742,659 A | 4/1998 | Atac et al. | 378/98.8 |
| 5,744,806 A | 4/1998 | Frojd | 250/370.09 |
| 5,751,783 A | 5/1998 | Granfors et al. | 378/108 |
| 5,757,011 A | 5/1998 | Whitebook et al. | 250/370.09 |
| 5,773,832 A | 6/1998 | Sayed et al. | 250/370.09 |
| 5,784,429 A | 7/1998 | Arai | 378/38 |
| 5,796,430 A | 8/1998 | Katoh et al. | 348/246 |
| 5,812,191 A | 9/1998 | Orava et al. | 348/308 |
| 5,828,720 A | 10/1998 | Syrjanen | 378/38 |
| 5,828,721 A | 10/1998 | Schulze-Ganzlin et al. | 378/38 |
| 5,864,146 A | 1/1999 | Karellas | 250/581 |
| 5,887,049 A | 3/1999 | Fossum | 378/98.8 |
| 5,892,227 A | 4/1999 | Schieber et al. | 250/370.12 |
| 5,912,942 A | 6/1999 | Schick et al. | 378/98.8 |
| 5,923,722 A | 7/1999 | Schulz | 378/98.8 |
| 5,930,330 A | 7/1999 | Wolfe et al. | 378/98.2 |
| 5,933,471 A | 8/1999 | Kalvin | 378/4 |
| 5,949,811 A * | 9/1999 | Baba et al. | 375/108 |
| 5,969,360 A | 10/1999 | Lee | 250/370.09 |
| 5,974,166 A | 10/1999 | Ino et al. | 382/132 |
| 6,002,742 A | 12/1999 | Nelvig | 378/98.8 |
| 6,035,012 A * | 3/2000 | Hsieh | 378/4 |
| 6,035,013 A | 3/2000 | Orava et al. | 378/37 |
| 6,047,042 A | 4/2000 | Khutoryansky et al. | 378/62 |
| 6,055,292 A | 4/2000 | Zeller et al. | 378/21 |
| 6,069,935 A | 5/2000 | Schick et al. | 378/98.8 |
| 6,081,739 A | 6/2000 | Lemchen | 600/407 |
| 6,093,019 A | 7/2000 | Morandi et al. | 433/29 |
| 6,094,468 A * | 7/2000 | Wilting et al. | 378/8 |
| 6,173,035 B1 | 1/2001 | Tachibana et al. | 378/39 |
| 6,208,710 B1 * | 3/2001 | Nagai | 378/108 |
| 6,233,310 B1 * | 5/2001 | Relihan et al. | 378/108 |

FOREIGN PATENT DOCUMENTS

| | | |
|---|---|---|
| WO | 93/00649 | 1/1990 |
| WO | 90/14793 | 12/1990 |
| WO | 91/15786 | 10/1991 |
| WO | 92/22188 | 12/1992 |
| WO | 93/00046 | 1/1993 |
| WO | 93/11707 | 6/1993 |
| WO | 93/14418 | 7/1993 |
| WO | 93/23952 | 11/1993 |
| WO | 94/12855 | 6/1994 |
| WO | 96/32064 | 10/1996 |
| WO | 98/56214 | 12/1998 |
| WO | 99/17659 | 4/1999 |
| WO | 99/62404 | 12/1999 |

* cited by examiner

FIG_1: System diagram

FIG_2a: AEC block diagram for panoramic projections

FIG_2b: AEC block diagram for cepahlographic projections

AUTOMATIC EXPOSURE CONTROL FOR DENTAL PANORAMIC AND CEPHALOGRAPHIC X-RAY EQUIPMENT

RELATED APPLICATION

This application is a continuation application to U.S. application Ser. No. 09/679,768 filed on Oct. 5, 2000, and claims the benefit of provisional application No. 60/158,706, filed Oct. 8, 1999.

BACKGROUND OF THE INVENTION

In dental panoramic and cephalographic radiography it is of utmost importance to ensure by an automatic method the optimal density of the latent image on the image detector, to allow proper detection of the anatomical details and consistency of the diagnostic outcome, and to minimise the need of repeating the x-ray examination so imparting unnecessary dose to the patient.

In dental panoramic radiography, using narrow beam scanning technique, the density is greatly influenced by (1) the individual patient characteristics (age, sex, race and size), particularly on the bone structure where osteoporosis phenomena may be present. Additionally (2) great variations in density occur during the exposure, caused by the different x-ray transmission of the various anatomical regions (temporo-mandibular joint, styloid process, hyoid bone, spine vertebrae, etc.) exposed during the scanning process. Finally (3) various irregularities in the patient denture (amalgam fillings, implants, missing teeth, etc.) may induce false detection and consequently erroneous operation of the automatic exposure control apparatus. While the automatic exposure control apparatus should effectively correct the density variations of the first two kinds, it is desirable that it has a high level of rejection for variations of the third kind (artefacts).

In cephalography, being a stationary radiographic technique, mainly density variations of the first kind are present, in conjunction also with the different patient projections (antero-posterior or latero-lateral).

One important feature is that the automatic exposure control apparatus can operate effectively in the several projection modalities (standard and child projections, transversal slicing, temporo-mandibular joint projections, sinus projections, frontal and orthogonal projections, cephalography antero-posterior and letero-lateral) as provided by the modern dental x-ray panoramic and cephalographic equipments.

Another desirable feature is that the automatic exposure control apparatus is able to compensate for the different sensitivities of the compatible image detectors (radiographic film speed factor, phosphor plate x-ray detectors, etc.).

Prior art automatic exposure apparatus for panoramic x-ray equipment determine imaging parameters (e.g. kV and mA of an x-ray tube, speed of the film drive or of the rotating arm supporting the x-ray tube and the film drive) by measuring the radiation passed through a patient either on the basis of a single sample taken at predefined imaging moment, or by continuous measurement, or by identification and measuring on a selected portion of the jaw (preferably the ramus of the mandibula).

Automatic exposure control by correction of the x-ray tube voltage (kV) is preferable, as it has faster response and provides x-ray energy modulation, with varying penetrating power. Adjustment of the speed of rotating arm or film drive requires huge computational capability, not practical in case of multi-projection equipment. Automatic exposure controls where adjustments are effected on the basis of a single sample are very sensitive to variations in the positioning of the patients and do not compensate for differences in the anatomy of the same. Automatic exposure apparatus with continuous control are very critical, due to the intrinsic difficulty in providing accurate and reproducible dynamic correction in all the anatomical regions, particularly in the spine, without producing asymmetry of the image density or other undesirable effects (vertical bands, artefact shadows, etc.). Identification of particular bone locations is restricted to regions with well defined anatomical structure and cannot be easily extended to varying anatomies as practically needed in multi-projection equipment.

SUMMARY OF THE INVENTION

The object of the invention is an automatic exposure control apparatus and method for dental panoramic and cephalographic x-ray equipment, capable of producing optimisation of the grey scale of the latent image in a consistent and reproducible way for all the available projections and regardless of the patient size and anatomy, providing high level of rejection of the artefacts generated by structures inserted into the patient denture.

The invention is founded on the following basic assumptions:

(a) in panoramic projections the optimal controlled parameter is the tube voltage (kV), for its faster dynamic response and varying penetrating power; in cephalographic projections the optimal controlled parameter is the exposure time, which is directly proportional to the output dose.

(b) both in panoramic and cephalographic projections it is preferable that the user selects the patient size, so pre-setting a programmed value of the controlled parameter.

(c) in panoramic projections, due to inherent criticality induced by the individual anatomic differences, the variance in positioning of the patient, the presence of irregular structures in the patient denture, it is wise to support the automatic exposure control operation with a variable kV profile pre-programmed for each available projection.

(d) for increased safety and reliability the automatic exposure control operates in a limited range around the programmed value (and programmed profile) of the controlled parameter.

Herefollowing is a description in greater detail of the invention, based on the exemplary embodiment illustrated in the attached drawings. By the disclosure and the appended claims the features and innovations of the invention will be outlined.

DESCRIPTION OF DRAWINGS AND TABLES

Table 1 shows the status of enable of the functional units in the different operational phases

DETAILED DESCRIPTION

Figure 1:
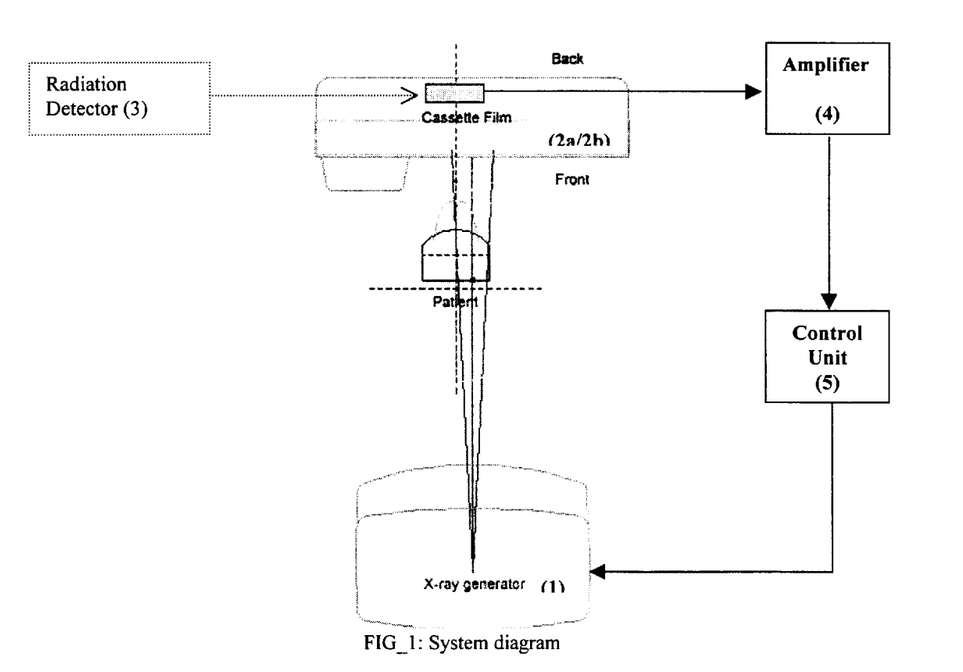
FIG. 1 is a system diagram showing a x-ray equipment incorporating the apparatus of the invention.

The x-ray diagnostic system illustrated in FIG. 1 is capable of performing dental panoramic radiography, using narrow beam scanning technique, transversal slicing radiography, using linear tomographic technique, and cephalography, using conventional x-ray technique.

It is equipped with a x-ray generator 1, mechanically coupled to the image receptor 2a by the rotating arm. The rotating arm rotates around the patient during the panoramic and transversal slicing scanning process. The image receptor is moved with variable speed during the panoramic sequence. The details of the panoramic technique are well known to those experienced in the matter, and will not further described.

In case of cephalography, the same x-ray generator 1 can be oriented towards a second image receptor 2b.

The Radiation Detectors 3, composed of one or more detectors such as photo diodes, are located behind the image detectors, one for panoramic and transversal slicing, and one for cephalography. The vertical and horizontal positions of the radiation detectors are located within the x-ray beam and are chosen to provide a signal corresponding to the absorption of the bone structure, namely the maxillary bone for the panoramic projections and the temporal bone for the cephalographic projection, which are of major diagnostic interest for the dentist.

The output signals of Radiation Detectors 3 are amplified by amplifiers 4 and the amplified signals are fed to the control unit 5.

The control unit 5 provides analog to digital conversion at fast rate (e.g. every 40 msec) of the measured value of radiation intensity, and correction of the exposure factors, e.g. the tube voltage, in synchronisation with the imaging process.

Figure 2A:
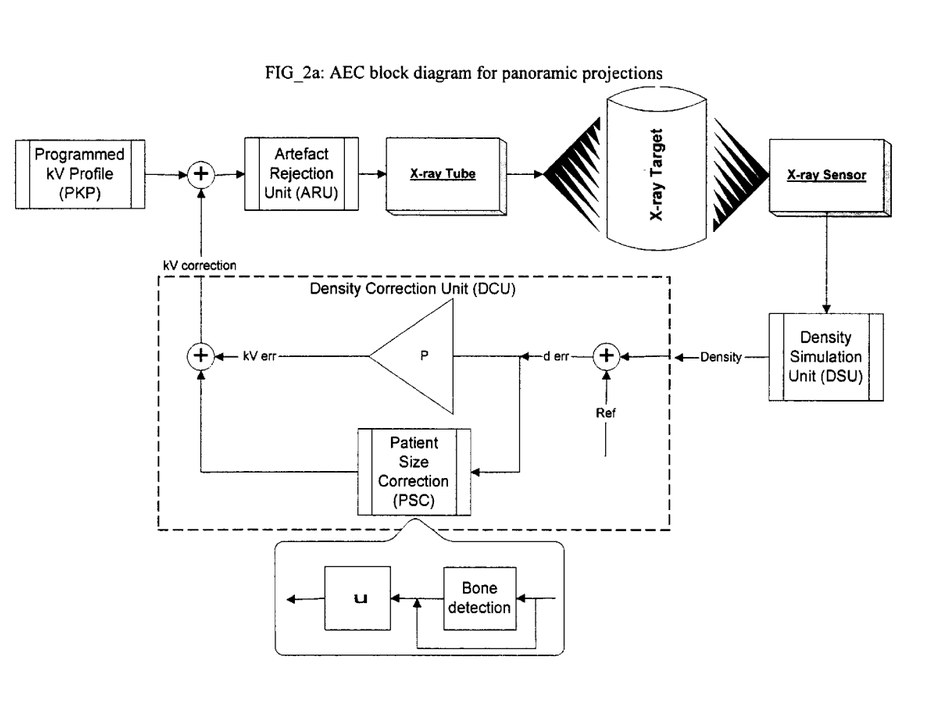
FIGS. 2a/2b is a block diagram showing the basic functional units of the apparatus of the invention.
Figure 2B:
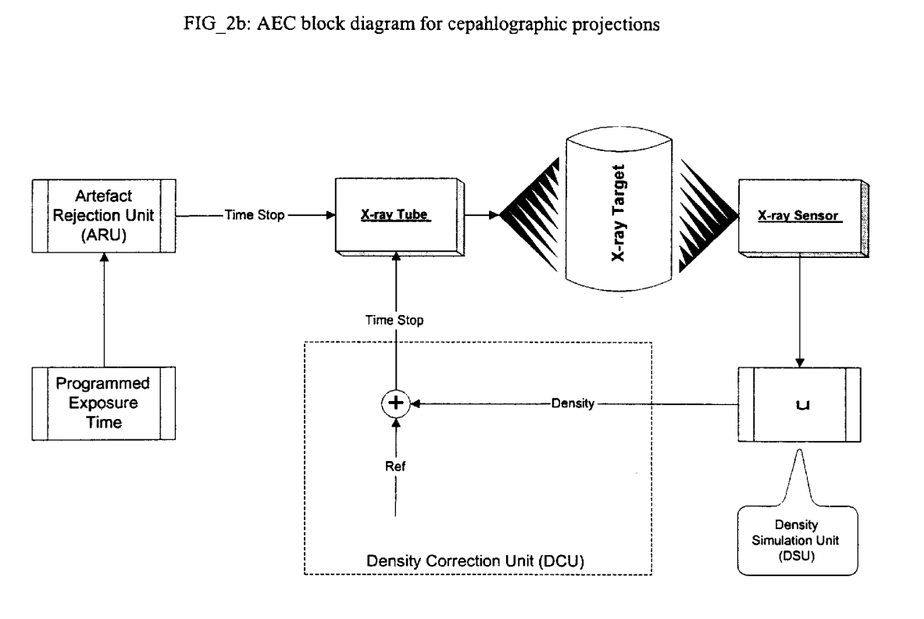

The automatic exposure control apparatus (herefollowing AEC) incorporates several functions, which are illustrated in FIG. 2 and are described below:

(a) PKP (Programmed kV Profile).

This functional unit is applicable only to panoramic projections. It provides a pre-programmed modulated profile of the tube voltage (kV) during the imaging process, to be used as a reference for the AEC operation in the panoramic projections. A different PKP may be available for each available projection, and eventually for each available patient size.

PKP has been implemented by adopting a tube voltage profile which has proven by test on phantom and in vivo to provide an optimised image density, e.g. at the roots of the teeth, along the various anatomical regions, such as the rami of the mandibula and the spine.

(b) DSU (Density Simulation Unit).

This functional unit provides simulation of the density of the latent image on the x-ray receptor. It processes the radiation detector amplified signal either by combining it with the speed of the cassette drive in case of panoramic projections, or by integrating it in the time in case of cephalographic projections.

Preferably the parameters of the simulation (i.e. the gain) are separately adjustable for each different projection and for the sensitivity of each different image detector type (e.g. the speed of the applied screen-film combination, or the phosphor plate sensitivity).

In order to introduce a safety control and inhibition of the AEC operation, upper and lower limits may be applied to the range of acceptable density values. Such limits may preferably be adjustable for each different projection.

(c) DCU (Density Correction Unit).

This functional unit processes the density simulation output generated by the DSU, by comparing it with a reference value and generating a density error. Then the computational unit translates the density error into a correction of the applicable imaging parameter.

In case of panoramic projections the density error is translated into a correction of the tube voltage, by applying to it a proportional control and/or an integrative control named PSC and described below. In panoramic projections such correction is applied with certain upper and lower limits over the Programmed kV Profile, as further described below within the ARU functional unit. Preferably the proportional control will be programmable for each projection.

In cephalographic projections the density error is translated into a correction of the exposure time, by comparing the actual integrated density level generated by the DSU with a threshold value, and generating a stop of x-ray emission in case that the threshold is exceeded.

(d) PSC (Patient Size Correction).

This functional unit is applicable only to panoramic projections. It performs on selected portions of the anatomy an integration of the density error generated by the DCU and generates in real-time a correction quantity to be added to the Programmed kV Profile.

The PSC function is intended to operate in a region of measurement corresponding to the anatomical region where there is a homogeneous bone structure to which the absorption characteristic of the patient can be correlated.

In a first embodiment the location of the region of measurement may be done by applying a pre-programmed interval, during which the density correction values within an acceptable range are integrated.

In another embodiment the start of the region of measurement may be located automatically during the imaging process, by performing an analysis of the density simulation generated by the DSU and its derivative, and identifying the negative transition of the derivative corresponding to start of the bone structure. After that the start of the region of measurement is identified, a pre-programmed interval is applied, during which the density correction values within an acceptable range are integrated.

The PSC operation is preferably adjusted for each projection, by using programmable parameters for the start and end of the seek zone, the gain of the integrator, and the range of acceptable values of samples.

(e) ARU (Artefacts Rejection Unit)

This functional unit operates both in panoramic and cephalographic projections. It aims to perform a rejection of spurious correction of the imaging parameter, as may be generated by artefacts of non-anatomical structures inserted into the patient denture, such as amalgam fillings, implants, etc.

In panoramic projections it analyses the correction of the imaging parameter generated by the DCU and its derivative, and rejects those samples exceeding threshold limits both in absolute value and in slew rate, by clipping them to a predefined level. The ARU operation is preferably adjusted for each panoramic projection, by using programmable threshold limits.

In cephalographic projections it prevents the exposure time to exceed a predefined maximum level, by generating a stop of x-ray emission when such maximum level would be exceed. The ARU operation is preferably adjusted for each cephalographic projection, by using a programmable exposure time limit as a percentage of the initial exposure time setting.

Figure 3:
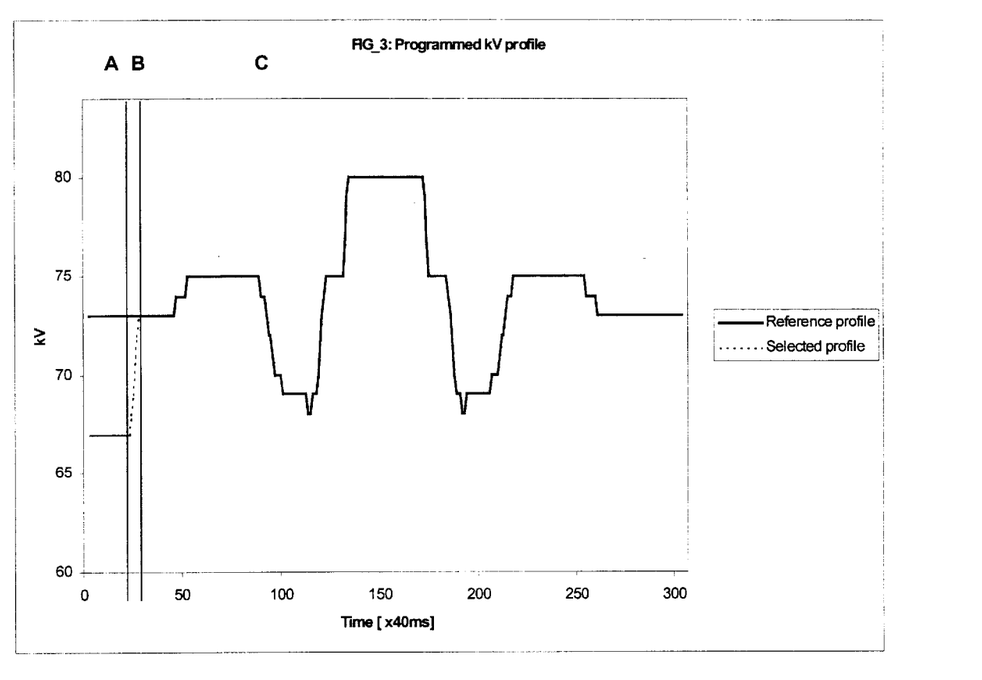
FIG. 3 is a plot showing an example of a programmed kV profile.

Based on the functional units above, the following operational phases are applicable in panoramic and transversal slicing projections:

A) Phase corresponding to the initial part of the imaging process, where the PKP corresponding the patient size selected by the user is applied, and the DSU, DCU and ARU functions are activated. The PSC control is inactive, while the P control (proportional) of the DCU may be active.

B) Phase where the PSC control is active, to provide a correction for the patient size. At the end of this phase the PKP will result shifted upwards or downwards depending on the values of the integrated samples. The PKP, DSU, DCU and ARU are active. The P control of the DCU may be inactive.

C) Phase where the PKP corrected with the additive term generated by the PSC is applied. The DSU, DCU and ARU functions are active. The PSC control is inactive, while the P control of the DCU may be active to provide further correction in specific anatomical regions, such as the spine.

The sequence of phases is illustrated in FIG. 3, together with an exemplary plot of the actual PKP. The status of enable of the functional units is illustrated in Table 1 below.

| Phase | PKP | DSU | DCU | ARU | PSC | P |
|-------|-----|-----|-----|-----|-----|---|
| A | Y | Y | Y/N | Y | N | Y/N |
| B | Y | Y | Y | Y | Y | Y/N |
| C | Y | Y | Y/N | Y | N | Y/N |

Y = ACTIVE
N = INACTIVE

In Cephalography the imaging parameters (tube voltage, tube current, exposure time) are predefined by the user through the user interface, either manually or pre-programmed depending on the selection of the patient size. Preferably the imaging parameters (i.e. the tube current) will be corrected depending on the sensitivity of the image detector (i.e. the speed of the film-screen combination). During the imaging process the tube voltage and current will stay stable at the values defined by the user, while the exposure time will be corrected by the AEC.

Figure 4:
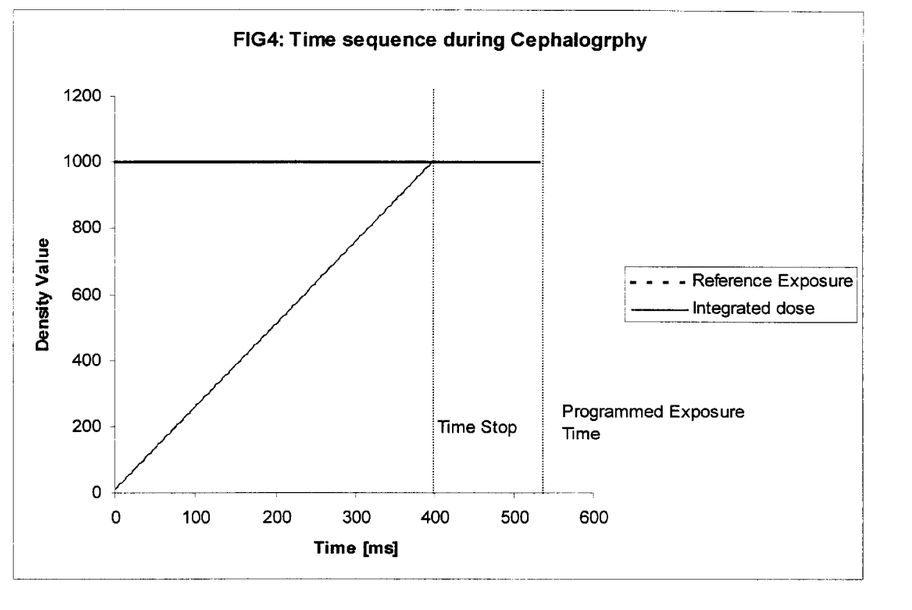
FIG. 4 shows the time sequence during Cephalography.

Based on the functional units above, the following operational phases are applicable in cephalographic projections:

A) Phase corresponding to the intial part of the imaging process. DSU, DCU and ARU are active. The density simulation generated by the DSU is analysed by the DCU and compared with the threshold value.

B) Phase corresponding to the stop of the exposure. If the integrated density simulation generated by the DSU is exceeding the threshold level, then the DCU generates the stop of the exposure. If the exposure time exceeds the programmed maximum limit then the ARU generates the stop of x-ray emission. After the end of exposure all functions get inactive.

The time sequence during Cephalography is illustrated in FIG. 4.

We claim:

1. A dental x-ray device having an x-ray radiation source and image receptors for panoramic and cephalographic radiography of bone structure of a patient, and for performing multiple projections where the density of the latent image is controlled by the imaging parameters, comprising an apparatus for the automatic control of the exposure (AEC) comprising:

an x-ray radiation detector located behind an image receptor and providing a signal corresponding to the x-ray absorption characteristic of the bone structure; a control unit for analysing the radiation detector signal and providing adjustment of the imaging parameters by incorporating as functional units:

(a) A programmed kV profile unit (PKP) being the functional unit providing pre-programmed modulated profile of the x-ray source tube voltage (kV) during the imaging process, correlated to the standard patient anatomy; said PKP being a reference for the AEC operation during the imaging process in the panoramic projections;

(b) a density simulation unit (DSU) being the functional unit providing simulation of the density of the latent image on the x-ray receptor, and processing a radiation detector-amplified signal by combining it with the speed of the cassette drive in case of panoramic projections, or by integrating it in the time in case of cephalographic projections;

(c) a density correction unit (DCU) being the functional unit processing the DSU density simulation output by comparing with a reference value, and generating a density error, and translating the density error into a correction of the applicable imaging parameter using a computational unit; in panoramic projections said density error is translated into a correction of the tube voltage, by applying to it a proportional control or an integrative control (PSC); in panoramic projections correction is applied with upper and lower limits over said PKP, within an ARU functional unit; in cephalographic projections said density error is translated into a correction of the exposure time, by comparing the actual integrated density level generated by the DSU with a threshold value, and generating a stop of x-ray emission when said threshold is exceeded;

(d) said PSC being a patient size correction functional unit operating in panoramic projections and performing on selected portions of the anatomy corresponding to a region of measurement an integration of the density error generated by the DCU and generating in real-time a correction quantity to be added to said PKP; in the region of measurement the density correction values are analysed and samples within a selected range are integrated;

(e) said ARU being an artefacts rejection unit and being a functional unit providing rejection of spurious correction of the imaging parameter, as generated by artefacts of non-anatomical structures inserted into the bone structure; in panoramic projections said ARU analyses the correction of the imaging parameter generated by the DCU and its derivative, and rejects samples exceeding threshold limits both in absolute value and in slew rate, by clipping them to a predefined level; in cephalographic projections it prevents the exposure time to exceed a predefined maximum level, by generating a stop of x-ray emission when such maximum level would be exceed.

2. A method for the automatic control of the exposure in panoramic projections employing the device of claim 1, comprising the steps of:

A) selecting by the user interface the patient size, by which the initial setting of the imaging parameter and the programmed kV profile (PKP) are defined;

B) initiating the imaging process, where the PKP corresponding the patient size selected by the user is applied; the DSU, DCU and ARU functions are active; the PSC control is inactive, while the P control (proportional) of the DCU may be active;

C) activating in the applicable region of measurement the PSC function, to provide a real time correction of the PKP corresponding to the actual patient size; at the end of this phase the PKP result is shifted upwards or downwards depending on the values of the integrated samples; the PKP, DSU, DCU and ARU are active; The P control of the DCU may be inactive;

D) disabling the PSC function, while the PKP corrected with the additive term generated by the PSC is applied; the DSU, DCU and ARU functions are active; the PSC control is inactive, while the P control of the DCU may be active to provide further correction in specific anatomical regions.

3. A method for the automatic control of the exposure in cephalographic projections employing the device of claim 1, comprising the steps of:

A) selecting through the user interface the imaging parameters (tube voltage, tube current, exposure time), manually or by pre-programmed control depending on the selection of the patient size;

B) initiating the imaging process, where the tube voltage and current are kept stable at the values pre-set by the user; DSU and DCU and ARU are active; the density simulation generated by the DSU is analysed by the DCU and compared with the threshold value;

C) Terminating the imaging process by generation of a stop of exposure signal; if the integrated density simulation generated by the DSU exceeds the threshold level, then the DCU generates the stop of the exposure; if the exposure time exceeds the programmed maximum limit then the ARU generates the stop of x-ray emission; and, after the end of exposure inactivating all functions.

4. The apparatus as set forth in claim 1 wherein a different PKP is programmable for each panoramic projection, and optionally for each patient size.

5. The apparatus and method as set forth in claim 1 wherein a range of acceptable density values is applied to the DSU density simulation, and such range of acceptable density values is programmable for each projection.

6. The apparatus and method as set forth in claim 1 wherein the parameters for the DSU simulation are programmable for each projection.

7. The apparatus and method as set forth in claim 1 wherein the parameters for the DSU simulation are programmable for each compatible image detector type, by taking into account its particular sensitivity.

8. The apparatus and method as set forth in claim 1 wherein the parameters for the DSU simulation are programmable for each compatible image detector holder type, by taking into account its particular x-ray transmission characteristic.

9. The apparatus and method as set forth in claim 1 wherein the parameters for the proportional control of the DCU correction are programmable for each projection.

10. The apparatus and method as set forth in claim 1 wherein the parameters for the PSC operation are programmable for each projection.

11. The apparatus and method as set forth in claim 1 wherein the start of the PSC region of measurement may be located automatically during the imaging process, by performing an analysis of the density simulation generated by the DSU and its derivative, and identifying the negative transition of the derivative corresponding to start of the bone structure.

12. The apparatus and method as set forth in claim 1 wherein the parameters for the ARU operation are programmable for each projection.

* * * * *